United States Patent [19]

Yamada et al.

[11] Patent Number: 4,762,839
[45] Date of Patent: Aug. 9, 1988

[54] QUINAZOLINONE COPMPOUNDS USEFUL FOR THE PROPHYLOXIS AND TREATMENT OF DIABETIC COMPLICATIONS

[75] Inventors: Yoshihisa Yamada, Kyoto; Yuzo Matsuoka, Toyonaka; Mamoru Matsumoto, Nara, all of Japan

[73] Assignee: Tanabe Seiyaku Co., Ltd., Japan

[21] Appl. No.: 866,226

[22] Filed: May 22, 1986

[30] Foreign Application Priority Data

Jun. 6, 1985 [JP] Japan .................. 60-124008
Oct. 18, 1985 [JP] Japan .................. 60-234160

[51] Int. Cl.⁴ .................. C07D 487/10; A61K 31/505
[52] U.S. Cl. .................. 514/259; 544/231; 5443/285; 548/485
[58] Field of Search .......... 514/259, 278; 544/230, 544/231; 546/18

[56] References Cited

U.S. PATENT DOCUMENTS

| | | | |
|---|---|---|---|
| 4,117,230 | 9/1973 | Sarges | 548/309 |
| 4,248,882 | 2/1981 | Sarges | 546/18 |
| 4,273,775 | 6/1981 | Sarges | 546/18 |
| 4,282,229 | 8/1981 | Sarsas | 514/278 |
| 4,533,667 | 8/1985 | Hutchison | 514/278 |
| 4,575,507 | 3/1986 | Lipinski | 514/278 |

FOREIGN PATENT DOCUMENTS

| | | |
|---|---|---|
| 53-653 | 5/1978 | Japan . |
| 95582 | 7/1979 | Japan . |
| 104876 | 8/1981 | Japan . |
| 45185 | 3/1982 | Japan . |

OTHER PUBLICATIONS

Chemie Berichte, vol. 103, 2394, (1970), by Capuano et al., ("Capuano et al. I").
Chemie Berichte, vol. 110, 3849, (1977), by Capuano et al., ("Capuano et al. II").

*Primary Examiner*—Robert Gerstl
*Assistant Examiner*—E. Bernhardt
*Attorney, Agent, or Firm*—Scully, Scott, Murphy & Presser

[57] ABSTRACT

Novel quinazolinone compounds of the formula:

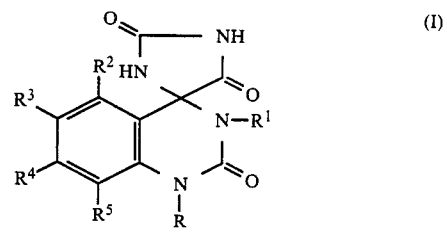

(I)

wherein R is hydrogen atom or a lower alkyl, $R^1$ is a lower alkyl, a substituted or unsubstituted phenyl or an aralkyl, and $R^2$, $R^3$, $R^4$ and $R^5$ are the same or different and are each hydrogen atom, a halogen atom, a lower alkyl, a lower alkoxy, a lower alkoxycarbonyl or a lower alkoxycarbonyl-lower alkenyl, or two adjacent groups of $R^2$, $R^3$, $R^4$ and $R^5$ when taken together form methylenedioxy and the other two are hydrogen atom, and a salt thereof, which are useful for the prophylaxis and treatment of various diabetic complications, and processes for the preparation thereof, and a pharmaceutical composition containing said compound as an active ingredient.

10 Claims, No Drawings

QUINAZOLINONE COMPOUNDS USEFUL FOR THE PROPHYLOXIS AND TREATMENT OF DIABETIC COMPLICATIONS

This invention relates to novel quinazolinone compounds and processes for the preparation thereof. More particularly, it relates to novel quinazolinone compounds of the formula:

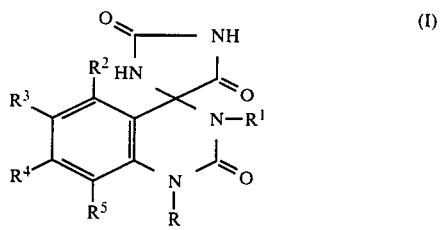

wherein R is hydrogen atom or a lower alkyl, $R^1$ is a lower alkyl, a substituted or unsubstituted phenyl or an aralkyl, and $R^2$, $R^3$, $R^4$ and $R^5$ are the same or different and are each hydrogen atom, a halogen atom, a lower alkyl, a lower alkoxy, a lower alkoxycarbonyl or a lower alkoxycarbonyl-lower alkenyl, or two adjacent groups of $R^2$, $R^3$, $R^4$ and $R^5$ when taken together form methylenedioxy and the other two are hydrogen atom, and a salt thereof, which are useful for the prophylaxis and treatment of various diabetic complications, and processes for the preparation thereof, and further a pharmaceutical composition containing said compound as an active ingredient.

PRIOR ART

It is known that diabetic complications include diabetic neurosis, diabetic cataract, diabetic microangiopathy such as diabetic retinopathy and diabetic nephrosis, and the like and that these diabetic complications are induced by accumulation of polyols such as sorbitol which are converted from hexose etc. by aldose reductase in vivo [cf. The New England Journal of Medicine, Vol. 288, 831–836 (1973)]. In order to prevent and treat the diabetic complications, there have hitherto been proposed various aldose reductase inhibitors which can inhibit the accumulation of polyols within the body, for instance, compounds having chromane nucleus (cf. Japanese Pat. First Publication Nos. 53653/1978 and 45185/1982, and U.S. Pat. No. 4,117,230), compounds having thiazolidine nucleus (cf. Japanese Patent First Publication No. 104876/1981), and compounds having phthalazine nucleus (cf. Japanese Patent First Publication No. 95582/1979).

Besides, there have been known some quinazolinone compounds, for instance, 3,1'-dimethyl-spiro[1,2,3,4-tetrahydroquinazoline-4,4'-imidazolidine]-2,2',5'-trione [cf. Chemie Berichte, Vol. 103, 2394 (1970)] and 3,1',3'-trimethyl-spiro[1,2,3,4-tetrahydroquinazoline-4,4'-imidazolidine]-2,2',5'-trione [cf. Chemie Berichte, Vol. 110, 3849 (1977)], but there has never been known any pharmacological activity of these quinazolinone compounds.

BRIEF DESCRIPTION OF THE INVENTION

The present inventors have extensively studied various spiro[1,2,3,4-tetrahydroquinazoline-4,4'-imidazolidine]compounds and pharmacological activities thereof and it has unexpectedly been found that the compounds of the formula (I) which have no substituent at 1'- and 3'- positions of known spiro[1,2,3,4-tetrahydroquinazoline-4,4'-imidazolidine] compounds have excellent aldose reductase inhibitory activity.

An object of the invention is to provide novel qunazolinone compounds having excellent aldose reductase inhibitory activity and hence being useful for the prophylaxis and treatment of diabetic complications. Another object of the invention is to provide processes for the preparation of said novel compounds. A further object of the invention is to provide novel intermediates useful for the preparation of said novel quinazolinone compounds. A still further object of the invention is to provide a pharmaceutical composition suitable for the prophylaxis and treatment of diabetic complications. These and other objects and advantages of the invention will be apparent to persons skilled in the art from the following description.

DETAILED DESCRIPTION OF THE INVENTION

The compounds of the invention have the formula (I) as mentioned hereinbefore.

The substituents on the formula (I) denote the following groups.

The term "lower alkyl" denotes a straight chain or branched chain alkyl having 1 to 5 carbon atoms, such as methyl, ethyl, n-propyl, isopropyl, n-butyl, isobutyl, sec.-butyl, tert.-butyl, or n-pentyl, isopentyl, etc. The term "lower alkoxy" denotes a straight chain or branched chain alkoxy having 1 to 5 carbon atoms, such as methoxy, ethoxy, n-propoxy, isopropoxy, n-butoxy, isobutoxy, sec.-butoxy, tert.-butoxy, n-pentyloxy, isopentyloxy, etc. The term "substituted or unsubstituted phenyl" denotes a phenyl or a phenyl substituted by a member selected from the group consisting of a lower alkyl and a halogen atom, such as an alkylphenyl having 1 to 5 carbon atoms in the alkyl moiety (e.g. methylphenyl, ethylphenyl, n-propylphenyl, isopropylphenyl, n-butylphenyl, n-pentylphenyl, etc.) and a halogenophenyl (e.g. chlorophenyl, fluorophenyl, bromophenyl). The term "aralkyl" denotes a phenylalkyl having 1 to 3 carbon atoms in the alkyl moiety, such as benzyl, phenethyl, etc. The term "halogen atom" denotes fluorine, chlorine, or bromine. The term "lower alkoxycarbonyl" denotes a straight chain or branched chain alkoxycarbonyl having 2 to 6 carbon atoms, such as methoxycarbonyl, ethoxycarbonyl, n-propoxycarbonyl, isopropoxycarbonyl, n-butoxycarbonyl, n-pentyloxycarbonyl, etc. The term "lower alkoxycarbonyl-lower alkenyl" denotes a straight chain or branched chain alkenyl having 2 to 6 carbon atoms which is substituted by the lower alkoxycarbonyl as set forth above, such as methoxycarbonylvinyl, ethoxycarbonylvinyl, n-propoxycarbonylvinyl, isopropoxycarbonylvinyl, n-butoxycarbonylvinyl, n-pentyloxycarbonylvinyl, etc.

Preferred groups for the substituents in the formula (I) are hydrogen and $C_{1-4}$ alkyl for R; $C_{1-4}$ alkyl, phenyl, $C_{1-4}$ alkyl-phenyl, halogenophenyl and phenyl-$C_{1-2}$ alkyl for $R^1$; and hydrogen, halogen, $C_{1-4}$ alkyl, $C_{2-5}$ alkoxycarbonyl, and $C_{2-5}$ alkoxycarbonyl-$C_{1-4}$ alkenyl for each $R^2$, $R^3$, $R^4$ and $R^5$, or methylenedioxy formed by adjacent two groups of $R^2$, $R^3$, $R^4$ and $R^5$.

Preferred compounds of the invention are compounds of the formula (I) wherein R is hydrogen or $C_{1-4}$ alkyl: $R^1$ is $C_{1-4}$ alkyl, phenyl, $C_{1-4}$ alkyl-phenyl, halogenophenyl, or phenyl-$C_{1-2}$ alkyl; and $R^2$, $R^3$, $R^4$ and $R^5$ are the same or different and are each hydrogen, halogen, $C_{1-4}$ alkyl, $C_{2-5}$ alkoxycarbonyl, or $C_{2-5}$ alkoxycarbonyl-$C_{2-4}$ alkenyl, or two adjacent groups of $R^2$, $R^3$, $R^4$ and $R^5$ when taken together form methylenedioxy and the other two are hydrogen.

Further preferred compounds of the invention are compounds of the formula (I) wherein R is hydrogen or $C_{1-4}$ alkyl; $R^1$ is $C_{1-4}$ alkyl, phenyl, $C_{1-4}$ alkyl-phenyl, halogenophenyl, or phenyl-$C_{1-2}$ alkyl; $R^2$ is hydrogen, halogen or $C_{1-4}$ alkyl; $R^3$ and $R^4$ are the same or different and are each hydrogen, halogen, $C_{1-4}$ alkyl, $C_{1-4}$ alkoxy, $C_{2-5}$ alkoxycarbonyl, or $C_{2-5}$ alkoxycarbonyl-$C_{2-4}$ alkenyl, or $R^3$ and $R^4$ when taken together form methylenedioxy; and $R^5$ is hydrogen or halogen.

Still further preferred compounds of the invention are compounds of the formula (I) wherein R is hydrogen, methyl or isobutyl $R^1$ is methyl, n-butyl, phenyl, methylphenyl, chlorophenyl, or benzyl $R^2$ is hydrogen, chlorine or methyl; $R^3$ and $R^4$ are the same or different and are each hydrogen, fluorine, chlorine, bromine, methyl, methoxy, ethoxycarbonyl, or ethoxycarbonyl-vinyl, or $R^3$ and $R^4$ when taken together form methylenedioxy and $R^5$ is hydrogen, fluorine or chlorine.

Particularly preferred compounds of the invention are compounds of the formula (I) wherein R is hydrogen or isobutyl; $R^1$ is methyl, n-butyl, phenyl, methylphenyl, chlorophenyl, or benzyl; $R^2$ is hydrogen or methyl $R^3$ is hydrogen, fluorine, chlorine, bromine, methyl or ethoxycarbonyl; $R^4$ is hydrogen, fluorine, chlorine, methyl or methoxy, or $R^3$ and $R^4$ when taken together form methylenedioxy; and $R^5$ is hydrogen, fluorine or chlorine.

In other preferred embodiment, R is hydrogen or $C_{1-4}$ alkyl; $R^1$ is $C_{1-4}$ alkyl; $R^2$ is hydrogen; $R^3$ is halogen; $R^4$ is hydrogen, halogen or $C_{1-4}$ alkyl; and $R^5$ is hydrogen or halogen. Particularly, R is hydrogen or isobutyl; $R^1$ is methyl; $R^2$ is hydrogen; $R^3$ is fluorine, chlorine or bromine; $R^4$ is hydrogen, chlorine or methyl; and $R^5$ is hydrogen or chlorine.

The compounds (I) of the invention have an asymmetric carbon in the molecule and hence may include two optical isomers. The present invention includes these optical isomers and racemic mixture thereof.

The compounds (I) of the invention can be prepared by various processes. For example, The compound (I) in which R is hydrogen atom can be prepared by subjecting the following compounds to cyclization reaction.

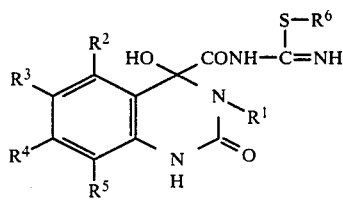

(II)

or

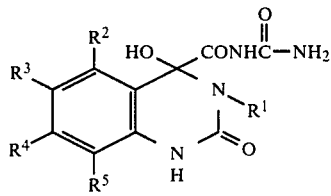

(III)

wherein $R^6$ is a lower alkyl, and $R^2$, $R^3$, $R^4$ and $R^5$ are the same as above.

The cyclization reaction of the compound (II) or the compound (III) can be carried out in an appropriate solvent at an elevated temperature. The cyclization of the compound (II) is preferably carried out in the presence of an acid (e.g. hydrochloric acid, hydrobromic acid, formic acid, etc.) at a temperature of 20° to 100° C., more preferably 60° to 90° C. The cyclization of the compound (III) is preferably carried out at a temperature of 150° to 250° C., more preferably 180° to 200° C. The solvent used in the cyclization of the compound (II) includes water, methanol, ethanol, dimethylformamide, 1,2-dichlorobenzene, and the like. The solvent used in the cyclization of the compound (III) includes 1,2-dichlorobenzene, nitrobenzene, naphthalene, biphenyl, and the like.

Alternatively, compounds of the formula:

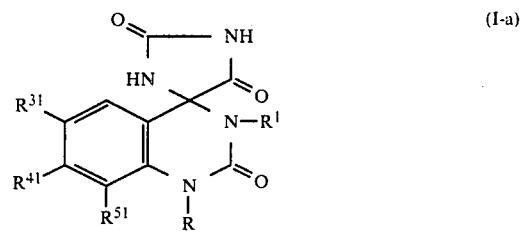

(I-a)

wherein $R^{31}$ is a halogen atom, $R^{41}$ is hydrogen atom or a lower alkoxy, $R^{51}$ is hydrogen atom or a halogen atom, and R and $R^1$ are the same as above, can be prepared by treating a compound of the formula:

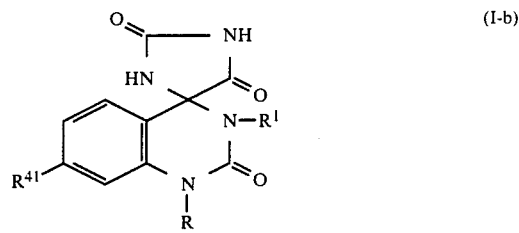

(I-b)

wherein R, $R^1$ and $R^{41}$ are the same as above, or a salt thereof with a halogenating agent.

The starting compound (I-b) may be used for the reaction in the form of a free base or of a salt thereof for instance, an alkali metal salt (e.g. sodium salt, potassium salt).

The treatment of the compound (I-b) with a halogenating agent can be carried out in an appropriate solvent. The halogenating agent includes sulfuryl chloride, chlorine, bromine, iodobenzene dichloride, N-bromosuccinimide, and the like. The solvent includes acetic acid, tetrahydrofuran, dioxane, water, or a mixture thereof. The reaction is preferably carried out at a temperature of 0° to 100° C., more preferably 20° to 70° C.

Besides, compounds of the formula:

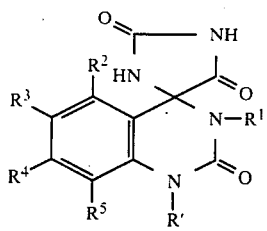
(I-c)

wherein R' is a lower alkyl, $R^1$, $R^2$, $R^3$, $R^4$ and $R^5$ are the same as above, can be prepared by reacting a compound of the formula:

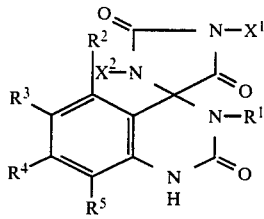
(IV)

wherein $X^1$ and $X^2$ are a protecting group, and $R^1$, $R^2$, $R^3$, $R^4$ and $R^5$ are the same as above, with an alkylating agent, such as a lower alkyl halide, and removing the protecting group, optionally followed by converting the resulting free base into a salt thereof.

In the starting compound (IV), the protecting groups $X^1$ and $X^2$ include any conventional protecting groups suitable for protecting an amino or imino group, for example, acetyl, benzyloxymethyl, benzoyl, benzyloxycarbonyl, tetrahydrofuranyl, and the like.

The alkylation of the compound (IV) with the lower alkyl halide is preferably carried out in an appropriate solvent in the presence of a base, such as sodium hydride, sodium hydroxide, potassium hydroxide, potassium carbonate, and the like. The solvent includes dimethylformamide, tetrahydrofuran, acetone, dimethylsulfoxide, and the like. The reaction is preferably carried out at a temperature of $-20°$ to $100°$ C.

The removal of the protecting group can be carried out by a conventional method suitable for each kind of the protecting groups, for example, by hydrolysis, electrolytic reduction, treatment with a base, treatment with an acid, catalytic reduction, oxidation and the like. The conversion of a free base into a salt can be carried out by a conventional method.

When the compounds (I) are obtained in the form of a racemic mixture, they can be resolved into each optical isomer by a conventional method. For instance, the optical resolution can be carried out by reacting the racemic mixture of the compounds (I) with a resolving agent in an appropriate solvent, isolating a hardly soluble diastereomeric salt in the form of a crystal and then isolating the soluble diastereomeric salt from the mother liquid by utilizing the difference in the solubility of the two diastereomeric salts. The resolving agent includes, for example, natural origin products such as brucine, quinine, cinchonidine, N-n-octylglucamine, dehydroabietylamine, etc., and optically active compounds such as α-methylbenzylamine, lysine, phenylalaninamide, tyrosine hydrazide, etc. The solvent includes methanol, ethanol, isopropanol, dioxane, tetrahydrofuran, water, or a mixture thereof. The diastereomeric salts thus prepared can be converted to the desired optically active compounds (I), for example, by treating with an acid (e.g. hydrochloric acid, hydrobromic acid, sulfuric acid, formic acid, etc.).

The starting compounds (II) and (III) used in the above reaction are also novel compounds. The compound (II) can be prepared, for example, by reacting a compound of the formula:

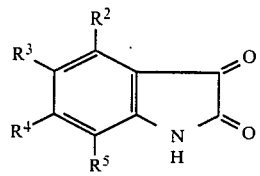
(V)

wherein $R^2$, $R^3$, $R^4$ and $R^5$ are the same as above, or a salt thereof (e.g. sodium salt, potassium salt, etc.) with a compound of the formula:

$$R^1NC=O \qquad (VI)$$

wherein $R^1$ is the same as above, in a suitable solvent (e.g. dimethylacetamide, dimethylformamide, etc.) in the presence of a base (e.g. triethylamine, etc.) at a temperature of $-20°$ to $50°$ C. to give a compound of the formula:

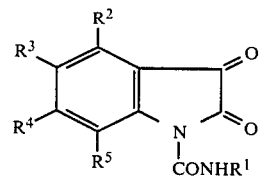
(VII)

wherein $R^1$, $R^2$, $R^3$, $R^4$ and $R^5$ are the same as above, and then reacting the compound (VII) obtained above with a compound of the formula:

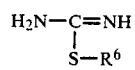
(VIII)

wherein $R^6$ is the same as above, or a salt thereof (e.g. hydrobromide, hydroiodide, sulfate, etc.) in a suitable solvent (e.g. tetrahydrofuran, etc.) in the presence of a base (e.g. triethylamine, etc.) at a temperature of $0°$ to $100°$ C.

The compound (II) can also be prepared by reacting the compound (VII) with thiourea in a suitable solvent (e.g. tetrahydrofuran, etc.) in the presence of a base (e.g. triethylamine, etc.) at a temperature of $0°$ to $100°$ C. to give a compound of the formula:

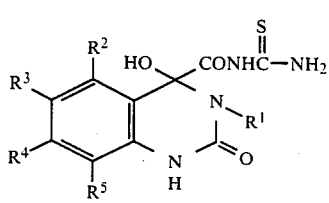
(IX)

wherein $R^1$, $R^2$, $R^3$, $R^4$ and $R^5$ are the same as defined above, and then reacting the compound (IX) obtained above with a compound of the formula:

$$R^6X \qquad (X)$$

wherein X is a halogen atom, and $R^6$ is the same as above, in a suitable solvent (e.g. dimethylformamide, etc.) in the presence of a base (e.g. sodium hydride, etc.) at a temperature of 0° to 50° C.

Besides, the compound (III) can be prepared, for example, by reacting the compound (VII) or a salt thereof with urea in a suitable solvent (e.g. tetrahydrofuran, etc.) in the presence of a base (e.g. 1,8-diazabicyclo[5.4.0]-7-undecene, etc.) at a temperature of 20° to 100° C.

The compounds (II) and (III) thus prepared can be used for the processes of the invention as they stands or after being purified by a conventional method.

The compounds (I) of the invention can be used as a medicament in the form of a free base or a pharmaceutically acceptable salt thereof. The pharmaceutically acceptable salt includes, for example, sodium salt, potassium salt, calcium salt, lysine salt, ethylenediamine salt, diethanolamine salt, and the like. These salts can easily be prepared by treating the free base of the compounds (I) with a base by a conventional method.

The compounds (I) and salts thereof have excellent aldose reductase inhibitory activity and hence are useful for the prophylaxis and treatment of various chronic symptoms associated with diabetes, i.e. diabetic complications, in warm-blooded animals, for example, diabetic neurosis, diabetic cataract, and diabetic microangiopathy such as diabetic retinopathy and diabetic nephrosis. The compounds (I) and salts thereof of the invention have also advantages that they have low toxicity and less neurotoxic side effects (e.g. dysbasia, areflexia, astasia, blepharoptosis, etc.).

The compounds (I) and salts thereof of the invention can be administered orally or parenterally. They can be administered in conventional pharmaceutical preparations, for example, tablets, granules, fine granules, powders, capsules, injections, eye drugs (e.g. eyewash, eye ointment, etc.), and the like. These preparations can be prepared by admixing the active compound (I) or salt thereof with conventional pharmaceutically acceptable carriers or diluents. The pharmaceutically acceptable carriers or diluents include excipients (e.g. sucrose, starches, mannitol, glucose, cellulose, talc, calcium phosphate, etc.), binding agents (e.g. methylcellulose, gelatin, gum arabic, polyethylene glycol, etc.), disintegrators (e.g. starches, carboxymethyl cellulose, sodium hydrogen carbonate, calcium phosphate, etc.), lubricants (e.g. magnesium stearate, talc, sodium laurylsulfate, etc.), preservatives (e.g. sodium benzoate, sodium hydrogen sulfide, etc.), stabilizers (e.g. citric acid, sodium citrate, etc.), and the like.

The dose of the compounds (I) and the pharmaceutically acceptable salts thereof may vary depending on the administration routes, ages, weight and states of the patients, severity of diseases, and the like, but is usually in the range of about 0.01 to 200 mg/kg/day, preferably 0.1 to 50 mg/kg/day.

The pharmacological activities of the compounds (I) and the salts thereof are illustrated by the following experiments.

EXPERIMENT 1

Aldose reductase inhibitory activity

Method:

Aldose reductase was obtained from lens of male rabbit (weighing 2.5–3.5 kg) in the same manner as described in J. Biol. Chem., Vol. 240, 877–882 (1965). The inhibitory activity of the test compounds against the aldose reductase was measured in the same manner as described in Biochim. Biophys. Acta., Vol. 128, 474–482 (1966). The aldose reductase inhibitory activity of the test compounds was shown by a concentration of the test compounds which was required for 50% inhibition of aldose reductase activity (i.e. 50% inhibitory concentration: $IC_{50}$).

| No. | Compound name |
|---|---|
| | Test compounds: |
| | (Compounds of the invention) |
| 1. | 6-Chloro-3-methyl-spiro[1,2,3,4-tetrahydroquinazoline-4,4'-imidazolidine]-2,2',5'-trione |
| 2. | d-6-Chloro-3-methyl-spiro[1,2,3,4-tetrahydroquinazoline-4,4'-imidazolidine]-2,2',5'-trione |
| 3. | 6-Chloro-3-methyl-spiro[1,2,3,4-tetrahydroquinazoline-4,4'-imidazolidine]-2,2',5'-trione-1'-sodium salt |
| 4. | d-6-fluoro-3-methyl-spiro[1,2,3,4-tetrahydroquinazoline-4,4'-imidazolidine]-2,2',5'-trione |
| 5. | 6-Chloro-3,7-dimethyl-spiro[1,2,3,4-tetrahydroquinazoline-4,4'-imidazolidine]-2,2',5'-trione |
| 6. | 6-Bromo-3-methyl-spiro[1,2,3,4-tetrahydroquinazoline-4,4'-imidazolidine]-2,2',5'-trione |
| 7. | 6,7-Dichloro-3-methyl-spiro[1,2,3,4-tetrahydroquinazoline-4,4'-imidazolidine]-2,2',5'-trione |
| 8. | 6,8-Dichloro-3-methyl-spiro[1,2,3,4-tetrahydroquinazoline-4,4'-imidazolidine]-2,2',5'-trione |
| 9. | 6-Fluoro-3-methyl-spiro[1,2,3,4-tetrahydroquinazoline-4,4'-imidazolidine]-2,2',5'-trione |
| 10. | 1-Isobutyl-6-chloro-3-methyl-spiro[1,2,3,4-tetrahydroquinazoline-4,4'-imidazolidine]-2,2',5'-trione |
| | (Reference compounds) |
| 11. | 3,1'-Dimethyl-spiro[1,2,3,4-tetrahydroquinazoline-4,4'-imidazolidine]-2,2',5'-trione [disclosed in Chem. Ber., 103, 2394 (1970)] |
| 12. | 3,1',3'-Trimethyl-spiro[1,2,3,4-tetrahydroquinazoline-4,4'-imidazolidine]-2,2',5'-trione [disclosed in Chem. Ber., 110, 3849 (1977)] |

Results:
The results are shown in Table 1.

| Test Compd. No. | Aldose reductase inhibitory activity $IC_{50}$ (M) |
|---|---|
| Compounds of the invention: | |
| 1 | $5.6 \times 10^{-8}$ |
| 2 | $2.2 \times 10^{-8}$ |
| 3 | $2.9 \times 10^{-8}$ |
| 4 | $6.4 \times 10^{-8}$ |
| 5 | $3.0 \times 10^{-8}$ |
| 6 | $5.2 \times 10^{-8}$ |
| 7 | $7.4 \times 10^{-8}$ |
| 8 | $3.7 \times 10^{-8}$ |
| 9 | $1.0 \times 10^{-7}$ |
| 10 | $2.7 \times 10^{-7}$ |
| Reference compounds | |
| 11 | $1.0 \times 10^{-5}$ |
| 12 | $>5 \times 10^{-5}$ |

EXPERIMENT 2

Inhibitory activity of accumulation of polyols

Method:

Slc:Wistar male rats (3–4 weeks old, one group: 3 rats) were fed with (i) a 20% galactose-added diet containing 20 mg % of a test compound (i.e. the test compound being contained in an amount of 20 mg per 100 g of the diet) (test compound-administered group), (ii) a 20% galactose-added diet (galactose control group), and (iii) a normal diet (no galactose) (normal control group) for 6 days. After the feeding, the rats were killed by cutting the carotid artery under ether anesthesia, and immediately, the sciatic nerves at both sides were taken out, and the amount of polyols accumulated in the sciatic nerves was measured by an acetyl-acetone method as described in Science, Vol. 182, 1146-1148 (1973). The polyol accumulation inhibition rate was calculated by the following equation.

$$\text{Polyol accumulation inhibition rate (\%)} = \left(1 - \frac{\left(\begin{array}{c}\text{Polyol amount (aver-}\\ \text{age) in test compd.-}\\ \text{administd. group}\end{array}\right) - \left(\begin{array}{c}\text{Polyol amount (aver-}\\ \text{age) in normal}\\ \text{control group}\end{array}\right)}{\left(\begin{array}{c}\text{Polyol amount (aver-}\\ \text{age) in galactose}\\ \text{control group}\end{array}\right) - \left(\begin{array}{c}\text{Polyol amount (aver-}\\ \text{age) in normal}\\ \text{control group}\end{array}\right)}\right) \times 100$$

Results:

As a result, the compounds of the invention used in Experiment 1 (i.e. Test Compound Nos. 1-10) showed all more than 50% of polyol accumulation inhibition rate.

EXPERIMENT 3

Acute toxicity and observation of symptoms

A suspension of the test compound in 0.5% carboxymethyl cellulose was orally administered to ddY male mice (weighing about 25 g, one group: 3 mice), and gross behavior and symptoms of the mice were observed for 14 days. As a result, in the mice administered with the compounds of the invention: d- and dl-6-chloro-3-methyl-spiro[1,2,3,4-tetrahydroquinazoline-4,4'-imidazolidine]-2,2',5'-trione no mouse died, and there was not observed any abnormal symptom such as dysbasia, areflexia, astasia, blepharoptosis, dyspnea, skin flush, lacrimation, etc.

The compounds (I) and their salts of the invention and preparation thereof are illustrated by the following Examples and Preparations.

EXAMPLE 1

5-Chloro-1-methylcarbamoylisatin (4.0 g) is dissolved in tetrahydrofuran (40 ml) and thereto are added 2-ethylisothiourea hydrobromide (4.0 g) and triethylamine (3.0 ml), and the mixture is stirred at room temperature for one hour. The reaction mixture is concentrated under reduced pressure to remove the solvent. To the residue [i.e. 6-chloro- 3-methyl-4-hydroxy-4-(2-ethylisothioureido)carbonyl-2-oxo-1,2,3,4-tetrahydroquinazoline] is added 10% hydrochloric acid (50 ml), and the mixture is stirred at 70°-80° C. for 3 hours. After cooling, the precipitates are taken by filtration to give 6-chloro-3-methyl-spiro[1,2,3,4-tetrahydroquinazoline-4,4'-imidazolidine]-2,2',5'-trione (2.5 g, yield 53.1%).

M.p. >280° C.

IR $\nu_{max}^{nujol}$ (cm$^{-1}$): 3300, 1780, 1740, 1718

MS (m/e): 280 (M$^+$)

NMR (DMSO-d$_6$) δ: 2.80 (3H, s), 6.92 (1H, d, J=9 Hz), 7.06 (1H, d, J=2 Hz), 7.40 (1H, d, d, J=9 Hz, J=2 Hz), 9.11 (1H, s), 10.07 (1H, s), 11.40 (1H, s)

EXAMPLES 2 to 22

In the same manner as described in Example 1, the corresponding starting compounds are treated to give the compounds as shown in Table 2.

TABLE 2

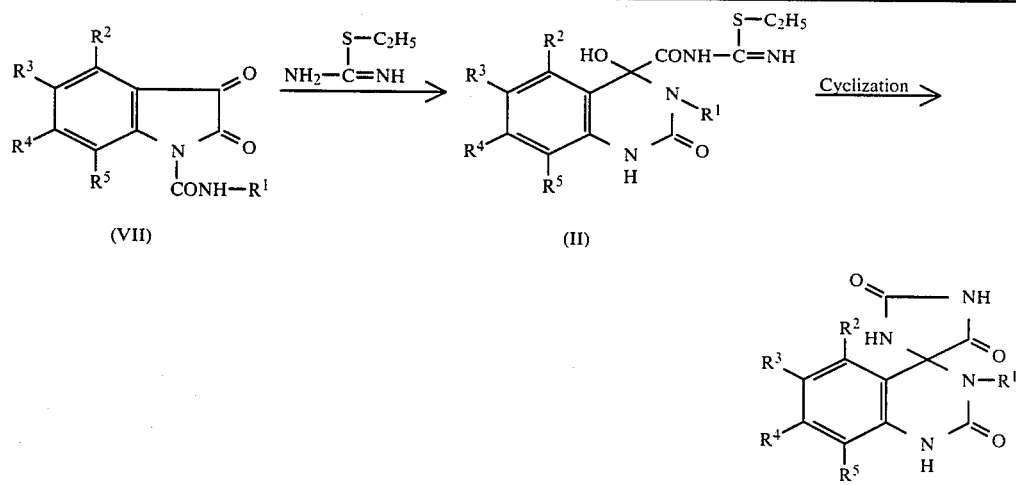

[I] (R$^1$ = CH$_3$, R$^5$ = H)

| Ex. No. | Compound (I) R$^2$ | R$^3$ | R$^4$ | Yield & M.p. | MS (m/e) | IR $\nu_{max}^{nujol}$ (cm$^{-1}$) | NMR (DMSO—d$_6$) δ: |
|---|---|---|---|---|---|---|---|
| 2 | H | F | H | >280° C. | 264(M$^+$) | 3280, 3190, 1783, 1735, 1657, 1610 | 2.78 (3H, s), 6.67-7.35 (3H, m), 9.03 (1H, s), 9.90 (1H, s), 11.31 (1H. s) |
| 3 | Cl | H | " | >280° C. | 280(M$^+$) | 3300, 2900, 1780, 1740, 1720, 1640 | 2.82 (3H, s), 6.87-7.40 (3H, m), 9.00 (1H, s), 10.20 (1H, s), 11.40 (1H, s) |
| 4 | H | " | Cl | 75% >280° C. | 280(M$^+$) | 3200, 2900, 1770, 1740, 1725, 1670 | 2.82 (3H, s), 6.90-7.30 (3H, m), 9.10 (1H, s), 10.08 (1H, s), 11.30 (1H, s) |
| 5 | " | CH$_3$O | H | 270- | 276(M$^+$) | | 2.80 (3H, s), 3.77 (3H, s), 6.50 (1H, |

TABLE 2-continued (VII) + NH$_2$—C(S—C$_2$H$_5$)=NH ⟶ (II) ⟶ Cyclization ⟶ (I)

| Ex. No. | R$^2$ | R$^3$ | R$^4$ | R$^5$ | Yield & M.p. | MS (m/e) | IR $\nu_{max}^{nujol}$ (cm$^{-1}$) | NMR (DMSO—d$_6$) δ: |
|---|---|---|---|---|---|---|---|---|
| | | | | | 272° C. | | | d, J=2 Hz), 6.67 (1H, d, d, J=9 Hz, J=2 Hz), 7.08 (1H, d, J=9 Hz), 9.10 (1H, s), 10.00 (1H, s), 11.45 (1H, s) |
| 6 | | H | CH$_3$ | H | 57.4% >280° C. | 260(M$^+$) | 3200, 1800, 1720, 1650, 1610 | 2.20 (3H, s), 2.79 (3H, s), 6.60–7.20 (3H, m), 8.94 (1H, s), 9.72 (1H, s), 11.20 (1H, s) |
| 7 | | " | —OCH$_2$O— | | >280° C. | 290(M$^+$) | 3400, 3180, 3070, 1789, 1715, 1680, 1642 | 2.76 (3H, s), 6.01 (2H, d, J=2 Hz), 6.45 (1H, s), 6.54 (1H, s), 9.00 (1H, s), 9.74 (1H, s), 11.30 (1H, s) |
| 8 | | " | Cl | CH$_3$ | 50.1% >280° C. | 294(M$^+$) | 3250, 3100, 1780, 1730, 1660, 1600 | 2.30 (3H, s), 2.80 (3H, s), 6.93 (1H, s), 7.10 (1H, s), 9.20 (1H, s), 10.11 (1H, s), 11.49 (1H, s) |
| 9 | | " | H | CH$_3$O | 270–272° C. | 276(M$^+$) | | 2.80 (3H, s), 3.77 (3H, s), 6.50 (1H, d, J=2 Hz), 6.67 (1H, d, d, J=9 Hz, J=2 Hz), 7.08 (1H, d, J=9 Hz), 9.10 (1H, s), 10.00 (1H, s), 11.45 (1H, s) |
| 10 | | " | " | CH$_3$ | 65% >280° C. | 260(M$^+$) | 3270, 1780, 1730, 1660, 1604 | 2.21 (3H, s), 2.72 (3H, s), 6.60–7.00 (3H, m), 8.90 (1H, s), 9.76 (1H, s), 11.15 (1H, s) |

[II] (R$^1$ = CH$_3$, R$^2$ = H)

| Ex. No. | R$^3$ | R$^4$ | R$^5$ | Yield & M.p. | MS (m/e) | IR $\nu_{max}^{nujol}$ (cm$^{-1}$) | NMR (DMSO—d$_6$) δ: |
|---|---|---|---|---|---|---|---|
| 11 | F | F | F | 55.3% >280° C. | | 3250, 3150, 3020, 1800, 1720 | 2.80 (3H, s), 7.07–7.40 (1H, m), 9.15 (1H, s), 10.35 (1H, s), 11.45 (1H, br) |
| 12 | H | H | F | 50.2% >280° C. | 264(M$^+$) | 3300, 3200, 3050, 1800, 1750, 1710 | 2.80 (3H, s), 6.70–7.40 (3H, m), 9.12 (1H, s), 10.00 (1H, s), 11.38 (1H, s) |

[III] (R$^1$ = CH$_3$, R$^5$ = H)

| Ex. No. | R$^2$ | R$^3$ | R$^4$ | Yield & M.p. | MS (m/e) | IR $\nu_{max}^{nujol}$ (cm$^{-1}$) | NMR (DMSO—d$_6$) δ: |
|---|---|---|---|---|---|---|---|
| 13 | H | Br | H | 50.4% >280° C. | 324(M$^{30}$) | 3250, 3100, 1775, 1730, 1650, 1600 | 2.79 (3H, s), 6.87 (1H, d, J=8 Hz) 7.15 (1H, d, J=2 Hz), 7.50 (1H, d, d, J=8 Hz, J=2 Hz), 9.12 (1H, s), 10.09 (1H, s), 11.50 (1H, br) |
| 14 | CH$_3$ | H | " | >280° C. | 260(M$^+$) | 3300, 2720, 1742, 1720, 1660, 1612 | 2.17 (3H, s), 2.80 (3H, s), 6.6–7.0 (2H, m), 7.1–7.5 (1H, m), 8.98 (1H, s) |
| 15 | H | Cl | CH$_3$O | 55% >280° C. | 310(M$^+$) | | 2.74 (3H, s), 3.80 (3H, s), 6.58 (1H, s), 6.98 (1H, s), 8.99 (1H, s) 9.90 (1H, s), 11.20 (1H, s) |
| 16 | " | COOC$_2$H$_5$ | H | 55.3% >280° C. | 318(M$^+$) | 3250, 1795, 1730, 1690, 1616 | 1.27 (3H, t, J=7 Hz), 2.78 (3H, s), 4.25 (2H, q, J=7 Hz), 6.93 (1H, d, J=9 Hz), 7.4–8.1 (2H, m), 9.09 (1H, s), 10.26 (1H, s), 11.33 (1H, s) |
| 17 | " | —CH=CH—COOC$_2$H$_5$ | " | >280° C. | 344(M$^+$) | 1795, 1740, 1678, 1658, 1615, 1603 | 1.23 (3H, t, J=7 Hz), 2.76 (3H, s), 4.13 (2H, q, J=7 Hz), 6.41 (1H, d, J=17 Hz), 6.84 (1H, d, J=9 Hz), 7.3–7.9 (2H, m), 7.56 (1H, d, J=17 Hz), 8.96 (1H, s), 10.07 (1H, s), 10.9–11.5 (1H, br) |

[IV] (R$^2$–R$^5$ = H)

TABLE 2-continued

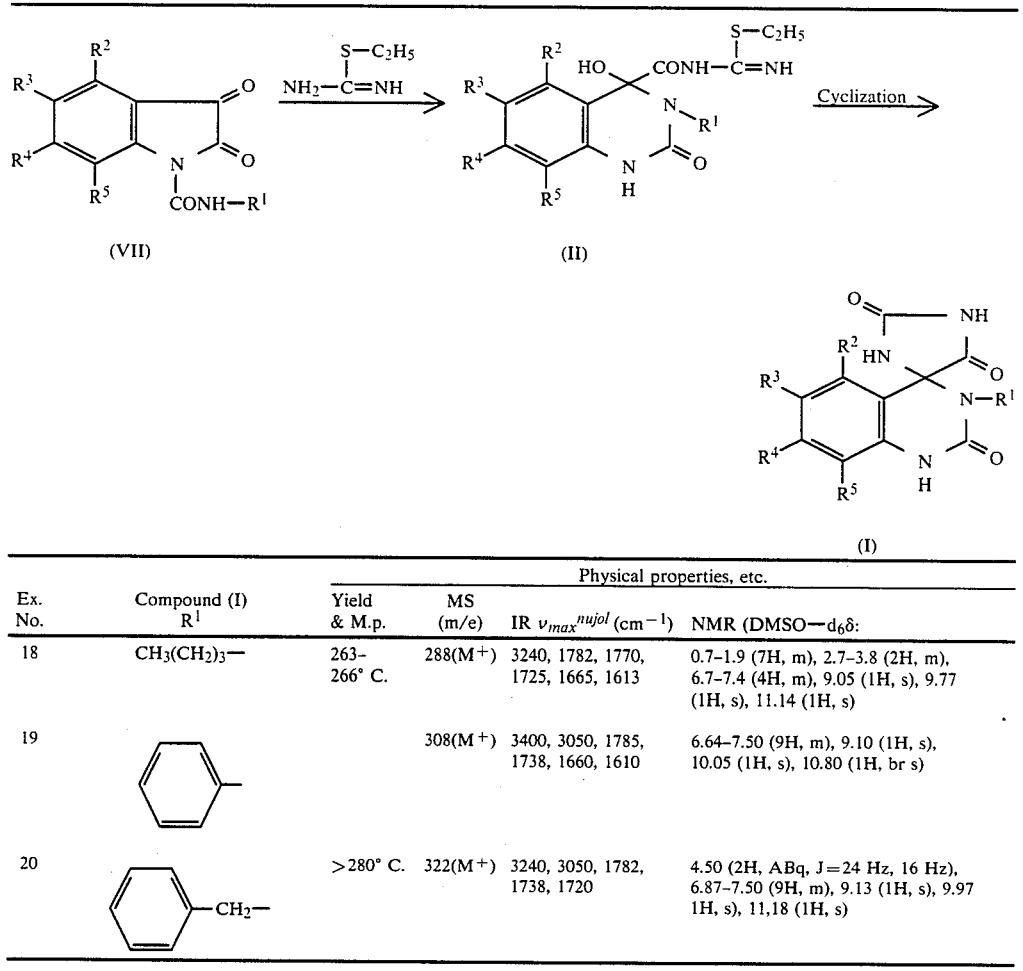

| Ex. No. | Compound (I) R¹ | Yield & M.p. | MS (m/e) | IR $\nu_{max}^{nujol}$ (cm$^{-1}$) | NMR (DMSO-d$_6$ δ: |
|---|---|---|---|---|---|
| 18 | CH$_3$(CH$_2$)$_3$— | 263–266° C. | 288(M$^+$) | 3240, 1782, 1770, 1725, 1665, 1613 | 0.7–1.9 (7H, m), 2.7–3.8 (2H, m), 6.7–7.4 (4H, m), 9.05 (1H, s), 9.77 (1H, s), 11.14 (1H, s) |
| 19 | (phenyl) | | 308(M$^+$) | 3400, 3050, 1785, 1738, 1660, 1610 | 6.64–7.50 (9H, m), 9.10 (1H, s), 10.05 (1H, s), 10.80 (1H, br s) |
| 20 | (phenyl)—CH$_2$— | >280° C. | 322(M$^+$) | 3240, 3050, 1782, 1738, 1720 | 4.50 (2H, ABq, J=24 Hz, 16 Hz), 6.87–7.50 (9H, m), 9.13 (1H, s), 9.97 1H, s), 11,18 (1H, s) |

EXAMPLE 21

3-Methyl-4-hydroxy-4-(2-ethylisothioureidocarbonyl)-2-oxo-1,2,3,4-tetrahydroquinazoline (2.0 g) is suspended in 10% hydrochloric acid (20 ml), and the mixture is stirred at 70°–80° C. for 3 hours. After cooling, the precipitates are taken by filtration and recrystallized from dimethylsulfoxide to give 3-methyl-spiro[1,2,3,4-tetrahydroquinazoline-4,4'-imidazolidine]-2,2',5'-trione (1.2 g).

M.p.>280° C.

IR $\nu_{max}^{nujol}$ (cm$^{-1}$): 3300, 3120, 3080, 1781, 1735, 1680, 1615

MS (m/e): 246 (M$^+$)

NMR (DMSO-d$_6$) δ: 2.80 (3H, s), 6.70–7.50 (4H, m), 9.05 (1H, s), 9.91 (1H, s), 11.31 (1H, s)

EXAMPLES 22 to 23

In the same manner as described in Example 21, the corresponding starting materials are treated to give the following compounds.

(22) 3-(4-Methylphenyl)-spiro[1,2,3,4-tetrahydroquinazoline-4,4'-imidazolidine]-2,2',5'-trione-½ HCON(CH$_3$)$_2$ M.p. 213°–215° C. (recrystallized from dimethylformamide-water)

IR $\nu_{max}^{nujol}$ (cm$^{-1}$): 1780, 1740, 1670, 1608

MS (m/e): 322 (M$^+$)

NMR (DMSO-d$_6$) δ: 2.32 (3H, s), 2.80 (3H, d, J=11 Hz), 6.80–7.60 (8H, m), 9.20 (1H, s), 10.08 (1H, s), 10.86 (1H, s)

(23) 3-(4-Chlorophenyl)-spiro[1,2,3,4-tetrahydroquinazoline-4,4'-imidazolidine]-2,2', 5'-trione.½ HCON(CH$_3$)$_2$ Yield: 82.7%

M.p.>280° C.

IR $\nu_{max}^{nujol}$ (cm$^{-1}$): 1788, 1740, 1662, 1610

MS (m/e): 342 (M$^+$)

NMR (DMSO-d$_6$) δ: 2.80 (3H, d, J=11 Hz), 6.90–7.70 (8H, m), 9.60 (1H, s), 10.20 (1H, s), 11.70 (1H, s)

EXAMPLE 24

(1) 5,6-Dichloro-1-methylcarbamoylisatin (9.6 g) is suspended in tetrahydrofuran (100 ml) and thereto are added thiourea (3.0 g) and triethylamine (5.6 ml), and the mixture is stirred at room temperature for 5 hours. The resulting precipitates are taken by filtration to give 6,7-dichloro-3-methyl-4-hydroxy-4-thioureidocarbonyl-2-oxo-1,2,3,4-tetrahydroquinazoline (4.1 g). M.p. 225°–228° C.

(2) 6,7-Dichloro-3-methyl-4-hydroxy-4-thioureidocarbonyl-2-oxo-1,2,3,4-tetrahydroquinazoline (2.8 g) is dissolved in dimethylformamide (30 ml), and thereto is added sodium hydride (60% oily suspension) (0.32 g), and the mixture is stirred at room temperature for 30 minutes. To the mixture is added ethyl bromide (2 ml), and the mixture is further stirred for 30 minutes, and then the solvent is distilled off under reduced pressure. To the residue [i.e. 6,7-dichloro-3-methyl-4-hydroxy-4-( 2-methylisothioureido)-carbonyl-2-oxo-1,2,3,4-tetrahydroquinazoline] is added 10% hydrochloric acid (30 ml), and the mixture is stirred at 70° C. for 4 hours. After cooling, the precipitates are taken by filtration, washed with 10% aqueous sodium hydrogen carbonate solution and then recrystallized from dimethylformamide-water to give 6,7-dichloro-3-methyl-spiro[1,2,3,4-tetrahydroquinazoline-4,4'-imidazolidine]-2,2',5'-trione (1.4 g).

IR $\nu_{max}^{nujol}$ (cm$^{-1}$): 3250, 1770, 1720, 1615, 1597

NMR (DMSO-d$_6$) δ: 2.78 (3H, s), 7.09 (1H, s), 7.29 (1H, s), 9.12 (1H, s), 10.18 (1H, s), 11.41 (1H, s)

EXAMPLE 25

3-Methyl-4-hydroxy-4-ureidocarbonyl-2-oxo-1,2,3,4-tetrahydroquinazoline (1.5 g) is added to 1,2-dichlorobenzene (30 ml), and the mixture is refluxed with stirring for 1.5 hour. After cooling, the precipitates are taken by filtration and recrystallized from dimethylsulfoxide to give 3-methyl-spiro[1,2,3,4-tetrahydroquinazoline-4,4'-imidazolidine]-2,2',5'-trione (0.8 g).

M.p.>280° C.

IR $\nu_{max}^{nujol}$ (cm$^{-1}$): 3300, 3120, 3080, 1781, 1735, 1680, 1615

MS (m/e): 246 (M$^+$)

NMR (DMSO-d$_6$) δ: 2.80 (3H, s), 6.70–7.50 (4H, m), 9.05 (1H, s), 9.91 (1H, s), 11.31 (1H, s)

EXAMPLE 26 d-3-Methyl-spiro[1,2,3,4-tetrahydroquinazoline-4,4'-imidazolidine]-2,2',5'-trione (17.24 g) is suspended in acetic acid (170 ml), and to the suspension is added dropwise sulfuryl chloride (8.54 ml), and the mixture is stirred at room temperature for 1.25 hour. The reaction mixture is poured into ice-water (500 ml), and the precipitates are taken by filtration. The crystals thus obtained are dissolved in ethanol (1 liter), and the undissolved materials are filtered off. The filtrate is treated with active carbon, and then the solvent is distilled off under reduced pressure. To the residue is added water, and the precipitates are taken by filtration, washed with water, and dried. The procedure is repeated additional one time to give d-6-chloro-3-methyl-spiro[1,2,3,4-tetrahydroquinazoline-4,4'-imidazolidine]-2,2',5'-trione monohydrate [this product has R-configuration at the 4-position of the quinazolinone skeleton] (14 g, yield: 71.3%).

IR $\nu_{max}^{nujol}$ (cm$^{-1}$): 3650, 3450, 3300, 3220, 3100, 1765, 1730, 1660, 1600

NMR (DMSO-d$_6$) δ: 2.80 (3H, s), 6.92 (1H, d, J=9 Hz), 7.06 (1H, d, J=2 Hz), 7.40 (1H, d, d, J=9 Hz, J=2 Hz), 9.11 (1H, s), 10.07 (1H, s), 11.40 (1H, s)

$[\alpha]_D^{20}$ =32.9° (c=1, ethanol)

EXAMPLES 27 to 29

In the same manner as described in Example 26, the corresponding starting materials are treated to give the compounds as shown in Table 4.

TABLE 4

(I-b)

(I-a)

| Ex. No. | Compound (I-a) | | | | Physical properties, etc. |
|---|---|---|---|---|---|
| | R$^1$ | R$^{31}$ | R$^{41}$ | R$^{51}$ | |
| 27*1 | CH$_3$ | Cl | H | H | Yield: 76.5%; M.p. 169–173° C.; $[\alpha]_D^{20}$ −33.7° (c=1, ethanol) |
| 28 | " | " | " | " | Yield: 71.4%; M.p. >280° C.; IR $\nu_{max}^{nujol}$ (cm$^{-1}$): 3300, 1780, 1740, 1718 |
| 29*2 | " | " | CH$_3$O | Cl | M.p. >280° C.; MS (m/e): 334 (M$^+$); IR $\nu_{max}^{nujol}$ (cm$^{-1}$): 3200, 1800, 1715, 1645 |

*1 This compound is a levo-rotatory isomer.
*2 The NMR spectrum data of this compound: NMR (DMSO—d$_6$) δ: 2.79 (3H, s), 3.82 (3H, s), 7.15 (1H, s), 9.10 (1H, s), 9.55 (1H, s), 11.38 (1H, s)

EXAMPLE 30

3-Methyl-spiro[1,2,3,4-tetrahydroquinazoline-4,4'-imidazolidine]-2,2',5'-trione (1.23 g) is dissolved in acetic acid (50 ml) and thereto are added iodine and sulfuryl chloride (4.0 ml), and the mixture is stirred at 60° C. for 90 hours. After cooling, water (100 ml) is added to the mixture, and the mixture is stirred under ice-cooling. The precipitates are taken by filtration. The crystals thus obtained are dissolved in aqueous sodium hydroxide and the undissolved materials are filtered off. The filtrate is neutralized with 10% hydrochloric acid, and the precipitates are taken by filtration, washed with water and dried to give 6,8-dichloro-3-methyl-spiro[1,2,3,4-tetrahydroquinazoline-4,4'-imidazolidine]-2,2',5'-trione (1.35 g, yield 85.4%).

M. p.>280° C.

IR $\nu_{max}^{nujol}$ (cm$^{-1}$) 3220, 1799, 1722, 1640

NS (m/e): 314 (M−1), 316 (M+1), 318 (M+3)

NMR (DMSO-d$_6$) δ: 2.77 (3H, s), 7.06 (1H, d, J=3 Hz), 7.59 (1H, d, J=3 Hz), 9.10 (1H, s), 9.53 (1H, s), 11.1–11.7 (1H, br)

EXAMPLE 31

6-Chloro-3-methyl-spiro[1,2,3,4-tetrahydroquinazoline-4,4'-imidazolidine]-2,2',5'-trione (1.4 g) is dissolved in 10.86% (w/w) aqueous sodium hydroxide and the solution is treated with active carbon and then concentrated under reduced pressure. The residue is crystallized from ethanol and then taken by filtration. The crystals thus obtained are washed with ethanol and isopropyl ether and dried to give 6-chloro-3-methylspiro[1,2,3,4-tetrahydroquinazoline-4,4'-imidazolidine]-2,2',5'-trione-1'-sodium salt (1.17 g, yield 77.3%).

IR $\nu_{max}^{nujol}$ (cm$^{-1}$) 3330, 3180, 1703, 1648

NMR (DMSO-d$_6$) δ: 2.62 (3H, s), 6.6–6.9 (2H, m), 7.0–7.5 (2H, m), 9.3–9.8 (1H, br)

EXAMPLE 32

In the same manner as described in Example 31, the corresponding starting material is treated to give the following compound:

(32) d-6-Chloro-3-methyl-spiro[1,2,3,4-tetrahydroquinazoline-4,4'-imidazolidine]-2,2',5'-trione-1'-sodium salt (yield 84.6%).

M.p. >280° C.

$[\alpha]_D^{20}$ +48.7° (c=1, water)

IR $\nu_{max}^{nujol}$ (cm$^{-1}$) 3620, 3300, 1708, 1683, 1645, 1600

NMR (DMSO-d$_6$) δ: 2.63 (3H, s), 6.72 (1H, d, J=10 Hz), 6.76 (1H, d, J=3 Hz), 7.13 (1H, d, d, J=10 Hz, J=3 Hz), 7.34 (1H, s), 9.57 (1H, s)

EXAMPLE 33

Isatin (294.3 g) is suspended in tetrahydrofuran (3 liter) and thereto are added with stirring triethylamine (279 ml) and methyl isocyanate (129.8 ml) at 15° C. The mixture is stirred at 20°–25° C. for 2.5 hours (1-methylcarbamoylisatin is produced in the mixture). To the reaction mixture are added 2-ethylisothiourea hydrobromide (444.2 g) and triethylamine (55.8 ml), and the mixture is refluxed for 2 hours. After cooling, the solvent is distilled off under reduced pressure. To the residue [i.e. 3-methyl-4-hydroxy-4-(2-ethylisothioureido)-carbonyl-2-oxo1,2,3,4-tetrahydroquinazoline] is added 10% hydrochloric acid (4 liter) and the mixture is stirred at 70° C. for 4 hours. After cooling, the precipitates are taken by filtration, washed with water, methanol (1 liter) and chloroform (1 liter) in this order and then dried to give 3-methyl-spiro[1,2,3,4-tetrahydroquinazoline-4,4'-imidazolidine]-2,2',5'-trione (369.2 g, yield 75%).

The physicochemical properties of this product are the same as those of the product prepared in Example 21.

EXAMPLE 34

(1) dl-3-Methyl-spiro[1,2,3,4-tetrahydroquinazoline-4,4'-imidazolidine]-2,2',5'-trione (12.3 g) and brucine dihydrate (21.5 g) are dissolved in a mixture (625 ml) of methanol and water (3:2 by volume) with heating. After the solution is allowed to cool, the precipitates are taken by filtration [the filtrate is referred to as "filtrate (I)"]. The crystals thus obtained are recrystallized from a mixture of methanol and water (3:2) to give d-3-methyl-spiro[1,2,3,4-tetrahydroquinazoline-4,4'-imidazolidine]2,2',5'-trione brucine salt (7.8 g).

$[\alpha]_D^{20}$ 67.0° (c=1, dimethylformamide)

The salt obtained above (7.8 g) is dissolved in water (20 ml), and thereto is added conc. hydrochloric acid (2 ml). The precipitates are taken by filtration and recrystallized from a mixture of methanol and water to give d-3-methyl-spiro[1,2,3,4-tetrahydroquinazoline-4,4'-imidazolidine]-2,2',5'-trione (2.3 g)

M.p. 174–176° C.

$[\alpha]_D^{20}$ +34.7° (c=1, ethanol)

(2) The filtrate (I) obtained in the above (1) is concentrated into dryness under reduced pressure, and the residue is dissolved in water (60 ml). The solution is neutralized with conc. hydrochloric acid (6 ml), and the precipitates are taken by filtration. The filtrate is distilled under reduced pressure to remove the solvent, and the precipitates are taken by filtration. The crystals are recrystallized from a mixture of methanol and water to give l-3-methyl-spiro[1,2,3,4-tetrahydroquinazoline-4,4'-imidazolidine]-2,2',5'-trione (2.1 g).

M.p. 174–176° C.

$[\alpha]_D^{20}$ 34.7° (c=1, ethanol)

EXAMPLE 35

(1) dl-6-Fluoro-3-methyl-spiro[1,2,3,4-tetrahydroquinazoline-4,4'-imidazolidine]-2,2',5'-trione (8.1 g) and quinine (prepared from 16.0 g of quinine hydrochloride) are dissolved in a mixture (450 ml) of methanol and water (2:1 by volume) with heating. After the solution is allowed to cool, the precipitates are taken by filtration [the filtrate is referred to as "filtrate (II)"]. Thus, there is obtained d-6-fluoro-3-methyl-spiro[1,2,3,4-tetrahydroquinazoline-4,4'-imidazolidine]-2,2',5'-trione quinine salt (4.0 g).

$[\alpha]_D^{20}$ −20.8° (c=1, dimethylformamide)

To the salt obtained above (4.0 g) is added 2% hydrochloric acid. The precipitates are taken by filtration and recrystallized from a mixture of methanol and water to give d-6-fluoro-3-methyl-spiro[1,2,3,4-tetrahydroquinazoline-4,4'-imidazolidine]-2,2',5'-trione (1.1 g)

M.p. 267° C.

$[\alpha]_D^{20}$ +37.6° (c=1, ethanol)

(2) The filtrate (II) obtained in the above (1) is regulated to pH 2 with 10% hydrochloric acid, and the precipitates are taken by filtration. The filtrate is neutralized with sodium hydrogen carbonate and extracted with ethyl acetate. The extract is distilled under reduced pressure to remove the solvent, and the residue is neutralized with 2% hydrochloric acid. The precipitates are taken by filtration and recrystallized from a mixture of methanol and water to give l-6-fluoro-3-methyl-spiro[1,2,3,4-tetrahydroquinazoline-4,4'-imidazolidine]-2,2',5'-trione (0.7 g).

M.p. 267° C.

$[\alpha]_D^{20}$ 39.6° (c=1, ethanol)

EXAMPLE 36

3'-Acetyl-1'-benzyloxymethyl-3-methyl-spiro[1,2,3,4-tetrahydroquinazoline-4,4'-imidazolidine]-2,2',5'trione (3.06 g) is dissolved in dimethylformamide (20 ml) and thereto is added methyl iodide (1 ml) and further added in portions sodium hydride (60%) (0.3 g) under ice-cooling, and the mixture is stirred at room temperature for 30 minutes. To the reaction mixture is added water, and the mixture is extracted with ethyl acetate. The extract is dried and distilled to remove the solvent. The residue is purified by silica gel column chromatography (solvent: chloroform) to give 3'-acetyl-1'-benzyloxymethyl-1,3-dimethyl-spiro[1,2,3,4-tetrahydroquinazoline-4,4'-imidazolidine]-2,2',5'-trione (3 g, yield: 94.5%) as an oily substance.

IR $\nu_{max}^{nujol}$ (cm$^{-1}$): 1800, 1720, 1640, 1600

(2) The above product (3.0 g) is dissolved in ethanol (20 ml) and thereto is added palladium black (0.2 g), and the mixture is subjected to catalytic reduction under hydrogen gas pressure (2–3 atmospheric pressure) for 5 hours. The catalyst is filtered off and the solvent is distilled off. The residue is dissolved in 10% aqueous sodium carbonate, and the mixture is heated at 60–80° C. for 30 minutes. The reaction mixture is neutralized with 10% hydrochloric acid, and the precipitates are taken by filtration and recrystallized from dimethylformamide-water to give 3'-acetyl-1,3-dimethylspiro[1,2,3,4-tetrahydroquinazoline-4,4'-imidazolidine]-2,2',5'-trione (0.85 g).

M.p. 261-263° C.

MS (m/e): 302 (M+)

IR $\nu_{max}^{nujol}$ (cm$^{-1}$): 1800, 1760, 1715, 1640

NMR (DMSO-d$_6$) δ: 2.40 (3H, s), 2.80 (3H, s), 3.36 (3H, s), 3.00-4.00 (1H, br), 6.90-7.60 (4H, m)

(3) The above product (1.0 g) is added to a sodium ethylate solution [prepared from metallic sodium (161 mg) and ethanol (20 ml)], and the mixture is stirred at room temperature for 3 hours. After the solvent is distilled off, the residue is neutralized with 10% hydrochloric acid, and the mixture is allowed to stand. The precipitates are taken by filtration and recrystallized from dimethylformamide-water to give 1,3-dimethyl-spiro[1,2,3,4-tetrahydroquinazoline-4,4'-imidazolidine]-2,2',5'-trione (500 mg) as colorless prisms.

M.p. 223-225° C.

IR $\nu_{max}^{nujol}$ (cm$^{-1}$): 3300, 3200, 1782, 1730, 1630

NMR (DMSO-d$_6$) δ: 2.86 (3H, s), 3.33 (3H, s), 7.00-7.63 (4H, m), 9.10 (1H, s), 11.40 (1H, br)

EXAMPLE 37

In the same manner as described in Example 36-(1), 3'-acetyl-1'-benzyloxymethyl-3-methyl-spiro[1,2,3,4-tetrahydroquinazoline-4,4'-imidazolidine]-2,2',5'-trione and isobutyl iodide are treated to give 3'-acetyl-1'-benzyloxymethyl-1-isobutyl-3-methyl-spiro[1,2,3,4-tetrahydroquinazoline-4,4'-imidazolidine]-2,2',5'-trione.

M.p. 70-72° C.

MS (m/e): 464 (M+)

NMR (DMSO-d$_6$) δ: 0.9-1.3 (6H, m), 1.9-2.3 (1H, m), 2.45 (3H, s), 2.84 (3H, s), 3.5-4.1 (2H, m), 4.68 (2H, s), 5.16 (2H, s), 6.6-7.1 (3H, m), 7.1-7.5 (4H, m)

The above product is treated in the same manner as described in Example 36-(2), (3) to give 1-isobutyl-3-methyl-spiro[1,2,3,4-tetrahydroquinazoline-4,4'-imidazolidine]-2,2',5'-trione.

M.p. 270° C.

MS (m/e): 302 (M+)

IR $\nu_{max}^{nujol}$ (cm$^{-1}$): 1790, 1723, 1645, 1608

NMR (DMSO-d$_6$) δ: 0.90 (6H, d, J=7 Hz), 1.8-2.3 (1H, m), 2.79 (3H, s), 3.6-4.0 (2H, m), 6.9-7.6 (4H, m), 9.02 (1H, s), 11.19 (1H, s)

EXAMPLE 38

1-Isobutyl-3-methyl-spiro[1,2,3,4-tetrahydroquinazoline-4,4'-imidazolidine]-2,2',5'-trione (0.76 g) as prepared in Example 37 is suspended in acetic acid (15 ml) and thereto are added sulfuryl chloride (0.3 ml) and a slight amount of iodine, and the mixture is stirred at room temperature for 19 hours. The reaction mixture is poured into ice-water, and the precipitates are taken by filtration and the crystals are dissolved in 10% aqueous sodium hydroxide. The undissolved materials are filtered off, and the filtrate is neutralized with 10% hydrochloric acid, and the precipitates are taken by filtration (this dissolution and precipitation procedure is repeated). The precipitates are taken by filteration and dried to give 6-chloro-1-isobutyl-3-methyl-spiro[1,2,3,4-tetrahydroquinazoline-4,4'-imidazolidine]-2,2',5'-trione (0.45 g).

M.p. 118° C.

MS (m/e): 338 (M$^{30}$+1), 336 (M+ −1)

IR $\nu_{max}^{nujol}$ (cm$^{-1}$): 1790, 1735, 1645, 1602

NMR (DMSO-d$_6$) δ: 0.90 (6H, d, J=7 Hz), 1.7-2.4 (1H, m), 2.79 (3H, s), 3.6-4.0 (2H, m), 7.03 (1H, d, J=3 Hz), 7.10 (1H, d, J=10 Hz), 7.40 (1H, d-d, J=10 Hz, J=3 Hz), 9.09 (1H, s), 11.26 (1H, s)

The preparation of the starting materials is illustrated below.

PREPARATION 1

A mixture of 5-fluoroisatin (9.9 g), triethylamine (1 ml) and dimethylformamide (30 ml) is stirred under ice-cooling, and thereto is added dropwise methyl isocyanate (3 g) at the same temperature. The mixture is stirred at room temperature for 30 minutes, and the precipitates are taken by filtration to give 5-fluoro-1-methylcarbamoylisatin (8.7 g). M.p. 230°-232° C.

PREPARATIONS 2 to 20

In the same manner as described in Preparation 1, the corresponding starting materials are treated to give the compounds as shown in Table 5.

TABLE 5

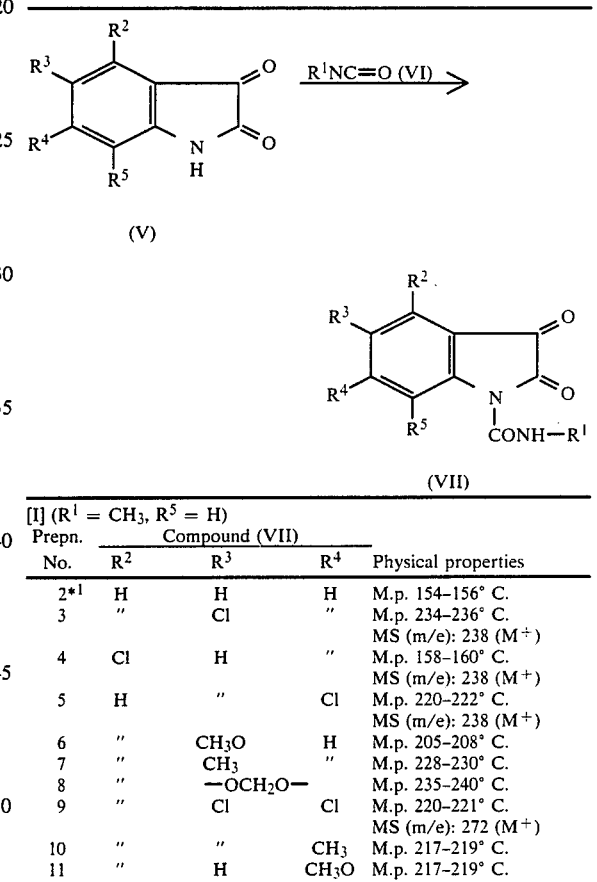

| [I] (R$^1$ = CH$_3$, R$^5$ = H) | | | | |
|---|---|---|---|---|
| Prepn. No. | Compound (VII) | | | Physical properties |
| | R$^2$ | R$^3$ | R$^4$ | |
| 2*1 | H | H | H | M.p. 154-156° C. |
| 3 | " | Cl | " | M.p. 234-236° C. MS (m/e): 238 (M+) |
| 4 | Cl | H | " | M.p. 158-160° C. MS (m/e): 238 (M+) |
| 5 | H | " | Cl | M.p. 220-222° C. MS (m/e): 238 (M+) |
| 6 | " | CH$_3$O | H | M.p. 205-208° C. |
| 7 | " | CH$_3$ | " | M.p. 228-230° C. |
| 8 | " | —OCH$_2$O— | | M.p. 235-240° C. |
| 9 | " | Cl | Cl | M.p. 220-221° C. MS (m/e): 272 (M+) |
| 10 | " | " | CH$_3$ | M.p. 217-219° C. |
| 11 | " | H | CH$_3$O | M.p. 217-219° C. |

| [II] (R$^1$ = CH$_3$, R$^2$ = H) | | | | |
|---|---|---|---|---|
| Prepn. No. | Compound (VII) | | | Physical properties |
| | R$^3$ | R$^4$ | R$^5$ | |
| 12 | H | H | CH$_3$ | M.p. 192-195° C. |
| 13 | F | F | F | M.p. 169-171° C. |
| 14 | H | H | F | M.p. 145-146° C. |

| [III] (R$^1$ = CH$_3$, R$^5$ = H) | | | | |
|---|---|---|---|---|
| Prepn. No. | Compound (VII) | | | Physical properties |
| | R$^2$ | R$^3$ | R$^4$ | |
| 15 | H | Br | H | M.p. 222-229° C. |
| 16 | CH$_3$ | H | " | NMR (DMSO—d$_6$) δ: 2.52 (3H, s), 2.87 (3H, d, J=5 Hz), 7.10 (1H, d, J=9 Hz), 7.57 (1H, t, J=9 Hz), 8.03 (1H, d, |

TABLE 5-continued

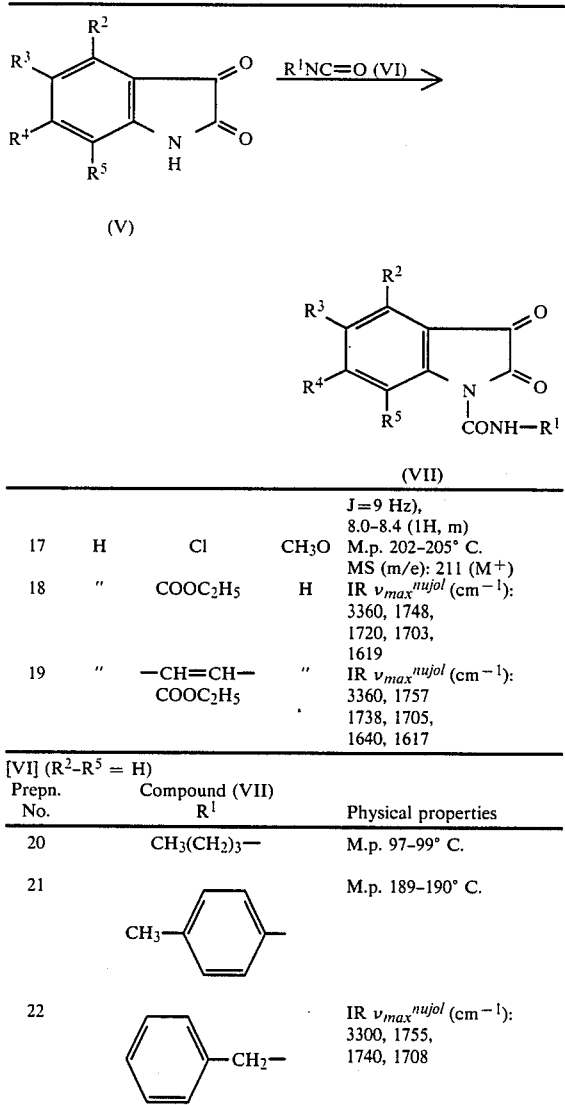

| | | | | J=9 Hz), 8.0-8.4 (1H, m) |
|---|---|---|---|---|
| 17 | H | Cl | $CH_3O$ | M.p. 202-205° C. MS (m/e): 211 (M+) |
| 18 | " | $COOC_2H_5$ | H | IR $\nu_{max}^{nujol}$ (cm$^{-1}$): 3360, 1748, 1720, 1703, 1619 |
| 19 | " | —CH=CH— $COOC_2H_5$ | " | IR $\nu_{max}^{nujol}$ (cm$^{-1}$): 3360, 1757 1738, 1705, 1640, 1617 |

| [VI] ($R^2$-$R^5$ = H) | | |
|---|---|---|
| Prepn. No. | Compound (VII) $R^1$ | Physical properties |
| 20 | $CH_3(CH_2)_3$— | M.p. 97–99° C. |
| 21 | $CH_3$-⌬- | M.p. 189–190° C. |
| 22 | 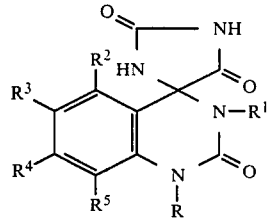 | IR $\nu_{max}^{nujol}$ (cm$^{-1}$): 3300, 1755, 1740, 1708 |

*[1]This compound is the same as the compound disclosed in Ann. Chem., 1974, page 2003.

PREPARATION 23 1-Methylcarbamoylisatin (8.16 g) is dissolved in tetrahydrofuran (100 ml), and thereto is added 2-ethylisothiourea hydrobromide (7.4 g), and the mixture is stirred at room temperature for 3 hours. The precipitates are taken by filtration, washed with water and dried to give 3-methyl-4-hydroxy-4-(2-ethylisothioureido)carbonyl-2-oxo-1,2,3,4-tetrahydroquinazoline (8.0 g). M.p.>280° C.

PREPARATIONS 24 to 25

In the same manner as described in Preparation 23, the corresponding starting materials are treated to give the following compounds.

(24) 3-(4-Methylphenyl)-4-hydroxy-4-(2-ethylisothioureido)carbonyl-2-oxo-1,2,3,4-tetrahydroquinazoline, M.p. 215°–218° C. (recrystallized from dimethylformamide-water)

(25) 3-(4-Chlorophenyl)-4-hydroxy-4-(2-ethylisothioureido)carbonyl-2-oxo-1,2,3,4-tetrahydroquinazoline, M.p. 223–224° C.

PREPARATION 26

1-Methylcarbamoylisatin (10.2 g) and 1,8-diazabicyclo[5.4.0]-7-undecene (0.3 g) are dissolved in tetrahydrofuran (100 ml), and thereto is added urea (4.5 g), and the mixture is refluxed for 10 hours. After cooling, the precipitates are taken by filtration, washed with water and methanol and recrystallized from a mixture of dimethylsulfoxide and ethanol to give 3-methyl-4-hydroxy-4-ureidocarbonyl-2-oxo-1,2,3,4-tetrahydroquinazoline, M.p.>280° C., MS (m/e): 246 (M+ —18)

PREPARATION 27

(1) 3-Methyl-spiro[1,2,3,4-tetrahydroquinazolidine-4,4'-imidazolidine]-2,2',5'-trione (7.38 g) is dissolved in dimethylformamide (60 ml), and thereto is added sodium hydride (60%) (1.2 g) at 15° C., and the mixture is stirred at room temperature for 30 minutes. To the mixture is added benzyloxymethyl chloride (4.71 g) at room temperature, and the mixture is further stirred at room temperature for 30 minutes. To the mixture is added water, and the mixture is extracted with ethyl acetate. The organic layer is washed with water, dried and then distilled to remove the solvent. The residue is crystallized from dimethylformamide-water to give 1'-benzyloxymethyl-3-methylspiro[1,2,3,4-tetrahydroquinazoline-4,4'-imidazolidine]-2,2'.5'-trione (10.4 g).

M.p. 226–227° C.

IR $\nu_{max}^{nujol}$ (cm$^{-1}$): 3200, 3050, 1800, 1735, 1660

(2) The product obtained above and acetyl chloride are treated in the same manner as described above (except that there is used isopropanol-isopropyl ether as a solvent for crystallization) to give 3'-acetyl-1'-benzyloxymethyl-3-methyl-spiro[1,2,3,4-tetrahydroquinazoline-4,4'-imidazolidine]-2,2',5'-trione (yield: 70%) M.p. 209–211° C.

What is claimed is:

1. A quinazolinone compound of the formula:

wherein R is hydrogen atom or lower alkyl, $R^1$ is a lower alkyl, and $R^2$, $R^3$, $R^4$ and $R^5$ are the same or different and are each hydrogen atom, a halogen atom, a lower alkyl or a lower alkoxy, or a salt thereof.

2. The compound as claimed in claim 1, wherein R is hydrogen of $C_{1-4}$ alkyl; $R^1$ is $C_{1-4}$ alkyl; and $R^2$, $R^3$, $R^4$ and $R^5$ are the same or different and are each hydrogen, halogen or $C_{1-4}$ alkyl.

3. The compound as claimed in claim 1, wherein R is hydrogen or $C_{1-4}$ alkyl; $R^1$ is $C_{1-4}$ alkyl; $R^2$ is hydrogen; $R^3$ is halogen; $R^4$ is hydrogen, halogen of $C_{1-4}$ alkyl; and $R^5$ is hydrogen or halogen.

4. The compound as claimed in claim 3, wherein R is hydrogen or isobutyl; $R^1$ is methyl; $R^2$ is hydrogen; $R^3$ is fluorine, chlorine or bromine; $R^4$ is hydrogen, chlorine or methyl; and $R^5$ is hydrogen of chlorine.

5. The compound as claimed, in claim 4, which is 6-chloro-3-methyl-spiro-[1,2,3,4-tetrahydroquinazoline-4,4'-imidaxolidine]-2,2',5'-trione or a salt thereof.

6. The compound as claimed in claim 4, which is d-6-chloro-3-methyl-spiro-[1,2,3,4-tetrahydroquinazoline-4,4'-imidazolidine]-2,2',5'-trione or a salt thereof.

7. An optically active isomer of the compound as set forth in claim 1.

8. The compound as claimed in claim 7, which is a dextro-rotatory isomer.

9. A pharmaceutical composition which comprises an effective amount of the compound as set forth in claim 1 in admixture with a conventional pharmaceutically acceptable carrier or diluent.

10. A method for treatment of diabetic complications in a warm-blooded animal which comprises administering to said warm-blooded animal an effective amount of the compound as set forth in claim 1.

* * * * *

UNITED STATES PATENT AND TRADEMARK OFFICE
CERTIFICATE OF CORRECTION

PATENT NO. : 4,762,839

DATED : August 9, 1988

INVENTOR(S) : Yoshihisa Yamada, et al.

It is certified that error appears in the above-identified patent and that said Letters Patent is hereby corrected as shown below:

In the Title: "COPMPOUNDS" should read as --COMPOUNDS--

Column 2, line 5: "qunazolinone" should read as --quinazolinone--

Column 7, line 64: "activity" should read as --activity:--

Column 11, line 52: "324($M^{30}$)" should read as --324($M^+$)--

Column 15, line 63: "$D^{20}$=32.9°" should read as --$D^{20}$+32.9°--

Column 19, line 65: "($M^{30}$+1)" should read as --($M^+$+1)--

Column 20, line 44: "MS(m/e):238 ($M^+$)" should read as --MS(m/e):211 ($M^+$)--

UNITED STATES PATENT AND TRADEMARK OFFICE
CERTIFICATE OF CORRECTION

PATENT NO. : 4,762,839

DATED : August 9, 1988

INVENTOR(S) : Yoshihisa Yamada, et al.

It is certified that error appears in the above-identified patent and that said Letters Patent is hereby corrected as shown below:

Column 22, line 68, Claim 4: "of" should read as --or--

Signed and Sealed this

Twelfth Day of December, 1989

Attest:

JEFFREY M. SAMUELS

Attesting Officer     Acting Commissioner of Patents and Trademarks